(12) United States Patent
Michailovna et al.

(10) Patent No.: US 7,611,716 B2
(45) Date of Patent: Nov. 3, 2009

(54) METHOD OF PROCESSING SEAWEED

(75) Inventors: Shevchenko Natalya Michailovna, Vladivostock (RU); Imbs Tatyana Igorevna, Vladivostok (RU); Urvantseva Angela Mikhailovna, Vladivostok (RU); Kusaykin Mikhail Igorevich, Vladivostok (RU); Kornienko Vladimir Gennadievich, Vladivostok (RU); Zvyagintseva Tatyana Nikolaevna, Vladivostok (RU); Elyakova Ljudmila Alexeevna, Moskow (RU)

(73) Assignee: Pacific Institute of Bioorganic Chemistry, Far East Branch of the Russian Academy of Sciences, Vladivostok (RU)

( * ) Notice: Subject to any disclaimer, the term of this patent is extended or adjusted under 35 U.S.C. 154(b) by 112 days.

(21) Appl. No.: 10/566,133

(22) PCT Filed: Jul. 23, 2004

(86) PCT No.: PCT/EP2004/008373
§ 371 (c)(1),
(2), (4) Date: Mar. 1, 2007

(87) PCT Pub. No.: WO2005/014657
PCT Pub. Date: Feb. 17, 2005

(65) Prior Publication Data
US 2007/0218076 A1 Sep. 20, 2007

(30) Foreign Application Priority Data
Jul. 28, 2003 (RU) ............................ 2003123744

(51) Int. Cl.
*A61K 36/00* (2006.01)
(52) U.S. Cl. .................................................. 424/195.17
(58) Field of Classification Search .................... None
See application file for complete search history.

(56) References Cited

U.S. PATENT DOCUMENTS
7,041,656 B2 * 5/2006 Sakai et al. ................ 514/61

FOREIGN PATENT DOCUMENTS

| | | |
|---|---|---|
| JP | 9173012 | 7/1997 |
| RU | 2028153 C1 | 2/1995 |
| RU | 2 070 808 C1 | 12/1996 |
| RU | 2078579 C1 | 5/1997 |
| RU | 2 132 622 C1 | 7/1999 |
| RU | 2 135 518 C1 | 8/1999 |
| RU | 2142812 C1 | 12/1999 |
| RU | 2194525 C1 | 12/2002 |
| WO | WO 02/086116 | * 10/2002 |

OTHER PUBLICATIONS

Zvyagintseva et al. (Comparative Biochemistry and Physiology Part C (2000), vol. 126, pp. 209-215).*
Zvyagintseva, T.N., et al.: "A New Procedure for the Separation of Water-Soluble Polysaccharides From Brown Seaweeds", Carbohydrate Research, vol. 332, No. 1-2, pp. 32-39, 1999.
Remedium, 4:49 (1992).
Zvyagintseva et al., "A new procedure for the separation of water-soluble polysaccharides from brown seaweeds", Carbohydrate Research, 322:32-39 (1999).
Nagumo et al., "Fucan Sulfates and Their Anticoagulant Activities", Polysaccharides in Medicine Applications, (Ed. S. Dumitriu), University of Sherbrooke, Quebec, Canada, N.-York-Basel-Hong Kong, (1996), p. 545-74.
Zhuang et al., Antitumor Active Fucoidan from the Brown Seaweed, *Umitoranoo (Sargassum thunbergii)*, Biosci. Biotechnol. Biochem., 59:563-567 (1995).
Beress et al., A New Procedure for the Isolation of Anti-HIV Compounds (Polysaccharides and Polyphenols) from the Marine Alga *Fucus vesiculosus*, Journal of Natural Products: 56(4):478-488 (Apr. 1993).
Hotimchenko et al., "Physicochemical properties, physiological activity and application alginate-polysaccharides of brown seaweed", Z. Biol morya (Russia), 27(3)-151-162 (2001).

* cited by examiner

*Primary Examiner*—Susan C Hoffman
(74) *Attorney, Agent, or Firm*—Morgan Lewis & Bockius LLP

(57) ABSTRACT

A method of processing seaweed, preferably a brown seaweed, comprises the following steps: (I) treating seaweed with an alcohol having one to six carbon atoms, preferably ethanol, to form an alcoholic fraction and an insoluble first seaweed residue; (II) separating the alcoholic fraction; (III) removing the alcohol from the alcoholic fraction to form a concentrate comprising biologically active low molecular weight compounds; (iv) extracting the first seaweed residue with an aqueous solution at a pH of less than 6 to form an aqueous first extract and an insoluble second seaweed residue; (v) optionally concentrating the first extract; and (vi) adjusting the pH of the resulting concentrated extract to a value in the range of 5 to 8 to obtain a first polysaccharide, fraction comprising a mixture of laminaran and fucoidan.

18 Claims, 2 Drawing Sheets

METHOD OF PROCESSING SEAWEED

This invention relates to a method of processing seaweed, to the product obtainable by the method and to the use of the product. In particular, the invention involves the processing of brown seaweed to obtain, preferably in a single process, extracts comprising acidic and neutral polysaccharides and an extract comprising low molecular weight biologically active compounds. The extracts can be used in medicine, food, perfumery, and in the cosmetic industry.

It is known that biologically active water-soluble polysaccharides can be obtained from brown seaweed (namely, laminarans and fucoidans). This method uses chromatographic separation of these polysaccharides on polytetrafluoroethylene (Russian patent application no 2135518 C1, 27 Aug. 1999). However, the method does not allow complete processing of brown seaweed. For example, polysaccharides, such as water-soluble mannuronans and alkali soluble alginates, cannot be isolated from seaweed by this method.

A method of complete processing of brown seaweed of the family Laminariceae is known. This method uses repeated treatment of seaweed with extraction solutions; precipitation by crystallization and filtration to obtain mannitol, alginic acid, alginate salts of calcium, sodium, potassium or ammonium, or mixed water-soluble salts of alginic acid with high thickening ability, and also a feed additive from seaweed waste (Russian patent application no 2070808, C1, 27 Dec. 1996). However, manufacturing alginates by this method has the disadvantage that biologically active water-soluble polysaccharides of brown seaweed get into the waste products.

A method of processing of brown seaweed, namely *Laminaria* sp. and *Fucus* sp., to obtain lipids and water-soluble concentrates is also known (Russian patent application no 2132622 C1, 10 Jul. 1999). The powder obtained from the water-soluble substances of the brown seaweed extract is a mixture containing polysaccharides, mannitol, vitamins and mineral substances. This method of treatment does not allow the isolation of individual polysaccharides such as fucoidan, laminaran, polymannuronate and alginate.

A method of isolating biologically active substances from *Laminaria* sp. (collected in the White Sea) uses the following sequence of operations: 1. the precipitation of a polysaccharide-protein complex from ethanol solution; 2. the precipitation of the laminaran and fucoidans complex; and 3. the separation of the complex into individual substances (Russian patent application no 2028153 C1, 9 Feb. 1995). However, as mentioned in that document, a number of the problems inherent in the technology for processing seaweed, as well as isolation of a polysaccharide-protein complex (laminaran and fucoidan) with one type of biological action (laxative effect), led to another method of isolation of the biologically active substances from *Laminaria* for medical purposes (Russian patent application no 2194525 C1, 20 Dec. 2002). The method includes the following operations: the raw material was dried, crushed, and defatted with chloroform and subsequently extracted with ethanol, hot water, and sodium carbonate. As a result, three products: mannitol, a total polysaccharide-protein complex and sodium alginate were obtained from one species of seaweed, namely *Laminaria saccharine* collected in the White Sea.

The problems of the aforesaid method are as follows: drying and defatting of seaweed with chloroform that leads to the removal of a valuable lipid complex; only mannitol can be isolated from the alcoholic extract and other low-molecular substances of seaweed are lost as waste products. The resulting polysaccharide-protein complex has a narrow spectrum of biological activities, namely detoxifying and laxative ones. This method does not allow the isolation of individual biologically active polysaccharides such as laminaran, fucoidan and polymannuronate.

It is known that polysaccharides of brown seaweed possess various biologically active properties that make preparations from seaweed promising for use in medicine. Fucoidans are found to be of anticoagulant, anticancer, hypolipidemic, antiviral activities (including against infection with HIV) (see: Nagumo, et al, "Fucan Sulfates and Their Anticoagulant Activities", In: Polysaccharides in Medicine Applications, (Ed. S. Dumitriu), University of Sherbrooke, Quebec, Canada, N.-York-Basel-Hong Kong, 1996, pages 545-57; Zhuang C et al, "Antitumor active fucoidan from the brown seaweed, umitoranoo (*Sargassum thunbergii*)", *Biosci. Biotechnol. Biochem.*, 1995, 59, 563-567; Beress et al, "A New Procedure for the Isolation of Anti-HIV Compounds (Polysaccharides and Polyphenols) from the brown seaweed *Fucus vesiculosus*", Natural Products-Lloydia, 1993, 56, 4, 478-488).

Laminaran is known to possess anticancer activity, polymannuronate is known to possesses anticancer and hypolipidemic activity.

At present, the applicant is not aware of any methods of complete processing of brown seaweed resulting in individual fucoidans, laminaran, polymannuronates, and alginates with standard characteristics. There are methods, such as disclosed in Russian patent application no 2194525 which obtain, in general, not individual preparations, but a mixture of polysaccharides. However, the physiological effects of mixtures of polysaccharides on an organism are different (see Hotimchenko et al, "Physicochemical properties, physiological activity and application alginate-polysaccharides of brown seaweed", *Z. Biol morya* (Russia), 2001, 27, 3, 151-162). Since it is difficult to obtain seaweed polysaccharides with standard characteristics, the application of these products as therapeutic agents in medicine is also a problem.

In the light of the above, it is an aim of the invention to develop a method of processing of brown seaweed to obtain individual preparations of acidic and neutral polysaccharides as well as concentrates of low molecular weight biologically active substances with standard characteristics useful in medicine, perfumery, and cosmetics.

According to the invention, there is provided a method of processing seaweed which comprises the following steps:
(i) treating seaweed with an alcohol having from one to six carbon atoms to form an alcoholic fraction and an insoluble first seaweed residue;
(ii) separating the alcoholic fraction;
(iii) removing the alcohol from the alcoholic fraction to form a concentrate comprising biologically active low molecular weight compounds;
(iv) extracting the first seaweed residue with an aqueous solution at a pH of less than about 6 to form an aqueous first extract and an insoluble second seaweed residue;
(v) optionally concentrating the first extract; and
(vi) adjusting the pH of the resulting concentrated extract to a value in the range of about 5 to about 8 to obtain a first polysaccharide fraction comprising a mixture of laminaran and fucoidan.

In another aspect, the present invention provides the product(s) obtainable by the method of the invention (such as the product of (iii) or (vi) above). The product may be obtained by the method of the invention.

A further aspect of the invention is a cosmetic or pharmaceutical composition, a food product, food supplement or a nutritional supplement comprising a product of the invention (i.e., a product obtainable or obtained by the method of the invention) together with a diluent or carrier. Diluents and carriers include those appropriate to the intended use of the composition. Thus, cosmetic compositions (which include perfumes) comprise a cosmetically acceptable diluent or carrier (such as an oil, water or ethanol), pharmaceutical compositions contain a pharmaceutically acceptable diluent or carrier (such as a sterile solvent), food products comprise components such as edible fats and/or oils and/or protein, and food supplements or nutritional supplements comprise carriers such as gelatin capsules in which the product is encapsulated.

In yet another aspect, the invention provides the use of a product of the invention in the cosmetic, pharmaceutical or food industry.

In one specific embodiment, the invention provides a method of complete processing of brown seaweed including the following steps:
  a) Seaweed is treated with ethanol; the extract obtained is separated; ethanol is then evaporated to obtain concentrate of biologically active low molecular weight compounds.
  b) The seaweed treated (as described above) is extracted again with hydrochloric acid (pH 2.0-2.5); the extract is concentrated by ultrafiltration, neutralized, and evaporated to obtain concentrate, containing a first polysaccharides fraction as a mixture of laminarans and fucoidans.
  c) The concentrate is neutralised, fucoidan (F1) and laminaran (L1) are sequentially precipitated with ethanol; the powders obtained are washed with ethanol and dried up.
  d) The seaweed treated (as described above) is extracted twice with hot water (pH 3.5-5.0).
  e) The extracts are combined and concentrated; the concentrate is evaporated to obtain a second polysaccharide fraction as a mixture of laminaran, fucoidan, and polymannuronic acid.
  f) The concentrate is acidified, polymannuronic acid is separated by centrifugation.
  g) The supernatant is dissolved in alkaline solution; salt of polymannuronic acid (M) is precipitated with ethanol; the powder is washed with ethanol and dried.
  h) The supernatant is neutralized and fucoidan (F2) and laminaran (L2) are sequentially precipitated with ethanol; the powder is washed with ethanol and dried.
  i) The remains of the seaweed are treated with alkali (pH 8-9), the extract is concentrated by ultrafiltration to precipitate a third polysaccharide fraction as a salt of alginic acid (A). The powder obtained is washed with ethanol and dried.

The method of the invention is preferably applied to the processing of species of brown seaweed, including brown seaweed from the Far East such as *Laminaria cichorioides* and/or *Laminaria japonica,* and/or *Alaria marginata,* and/or *Alaria fistulosa,* and/or *Fucus evanescens,* and/or *Undaria pinnatifida.* However, the method can be applied to process other species of seaweed. In each specific case, a different yield of acidic and neutral polysaccharides with different monosaccharide composition will be obtained.

The method preferably uses fresh or frozen seaweed. This is advantageous because polyphenols and carotenoids are easily oxidised when drying seaweed. Using this method, there is no need to include a stage of crushing seaweed as after deep freezing with the subsequent refreezing, cell substances of whole seaweed are more fully extracted.

Preferably, the method of the invention comprises first steps of preparing the seaweed comprising removing any small shells or other solid phase impurities and, optionally, washing. The seaweed may be mechanically treated, such as by grinding, comminuting or otherwise reducing the size of the seaweed. Preferably, the seaweed is not treated with a non-polar solvent, such as chloroform prior to treatment with the alcohol.

Preferably, the alcohol that is used in the method is ethanol. Preferably, fresh or frozen seaweed is treated with ethanol, such as for 20 to 24 h, more preferably at a temperature of about 40-60° C. After this treatment, the alcoholic extract is removed from the insoluble seaweed residue, (also referred to herein as the "first insoluble seaweed residue"), for example by decanting or filtration, and the alcohol is evaporated to obtain a concentrate comprising biologically active low molecular weight compounds. The low molecular weight compounds preferably have a molecular weight of less than about 1,500 Da, more preferably about 100 to 1,000 Da, for example 200 to 700 Da. The concentrate comprises polyphenols, mannitol, carotenoids, amino acids, oligosaccharides, iodine, mineral salts and B-vitamins. This extract can be applied in the perfumery and/or cosmetic industry.

The first seaweed residue is then further treated. The first seaweed residue is optionally dried, extracted with an aqueous solution having a pH of less than about 6 (e.g., pH 0.5-3, such as 0.5-1.5), for example with a dilute solution of hydrochloric acid, preferably for 10-14 h at 20-25° C. with stirring. The insoluble material remaining after this extraction is termed herein the "second seaweed residue". The extract is preferably further concentrated by ultrafiltration on hollow fiber with pore size of 5 kDa, neutralized with a solution of hydroxide sodium up to pH 6.0, and evaporated. A concentrate of a first polysaccharide fraction, comprising a mixture of laminaran and fucoidan, is obtained. The concentrate is optionally neutralized, following which fucoidan may be precipitated with ethanol (preferably two volumes), the resulting powder is optionally washed with ethanol and dried. As a result, a preparation of fucoidan can be obtained from the first polysaccharide fraction. Laminaran may be precipitated from the solution, for example by the addition of ethanol (preferably two volumes once again). The resulting powder obtained is optionally washed with ethanol and dried.

The second seaweed residue may be optionally further extracted with hot water. The residue after extraction is referred to herein as the "Third seaweed residue". Preferably, the extraction is carried out at pH 3.5-4.0, more preferably using a first extraction for 2-4 h and a second extraction for 1-2 h. The extract (after having being combined, if appropriate) is preferably concentrated by ultrafiltration on hollow fiber with pore size of 15 kDa, and the concentrate is then evaporated. The resulting fraction, referred to herein as the "second polysaccharide fraction" comprises a mixture of laminarans, fucoidans and polymannuronic acid. The extract is optionally then acidified to pH 2.0-2.5 and a precipitate comprising polymannuronic acid can be separated, for example by centrifugation. To obtain a salt of polymannuronic acid, the precipitate can be dissolved in a minimal volume of sodium hydroxide or ammonium oxalate, or calcium hydroxide, or magnesium hydroxide. The solution is then optionally neutralized and the polymannuronic acid salt may be precipitated, preferably using ethanol (e.g., two volumes). The precipitate is optionally washed with ethanol and dried. As a result, a preparation comprising polymannuronates can be obtained.

The supernatant, which remains after separation of the polymannuronic acid, can be neutralized and a fucoidan fraction can be precipitated by the addition of ethanol (e.g., two volumes). The resulting precipitate is optionally washed with ethanol and dried. Thus, a preparation comprising fucoidan can be obtained. Laminaran can subsequently be precipitated from the solution, for example by the addition of more ethanol, such as two more volumes of ethanol. The precipitate is optionally washed with ethanol and dried. As a result, a preparation comprising laminaran can be obtained.

To obtain a salt of alginic acid, the third seaweed reside may be treated with an alkaline solution, such as of sodium hydroxide, or ammonium hydroxide, or calcium hydroxide, or magnesium hydroxide, more preferably at pH 8-9, for example for 2-4 h at temperature of 55-65° C. The resulting extract is then optionally concentrated by ultrafiltration on a membrane with pores of 100 kDa, neutralized, and a third polysaccharide fraction (comprising alginic acid salt) can be precipitated, for example using ethanol. The precipitate is optionally washed with ethanol and dried. As a result, a preparation comprising alginate can be obtained.

The method of the invention allows seaweed to be processed to obtain a range of different fractions and extracts, including polysaccharides with standard characteristics. The preparations of acidic and neutral polysaccharides obtained in the invention can be applied in medicine as therapeutic agents. Standard characteristics of these preparations are given in the examples.

The method of the invention also allows a concentrate rich in biologically active low molecular weight compounds to be obtained. This concentrate can be used in perfumery and in the cosmetic industry. These concentrates can also be used to obtain individual substances.

After isolation of the concentrates and polysaccharides, the remains of seaweed can be used as a feed additive.

The method is readily industrially applicable as it includes basic steps of extraction, ultracentrifugation, and fractional precipitation of the final products. Using the latter procedure, the first and second polysaccharide fractions can be fractionated very quickly into individual preparations: fucoidan, laminaran, and polymannuronic acid, as well as different products (depending on the species of seaweed). A good yield can be obtained. The ethanol and/or other alcohol can be distilled and recycled in the method.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

Figure 1:
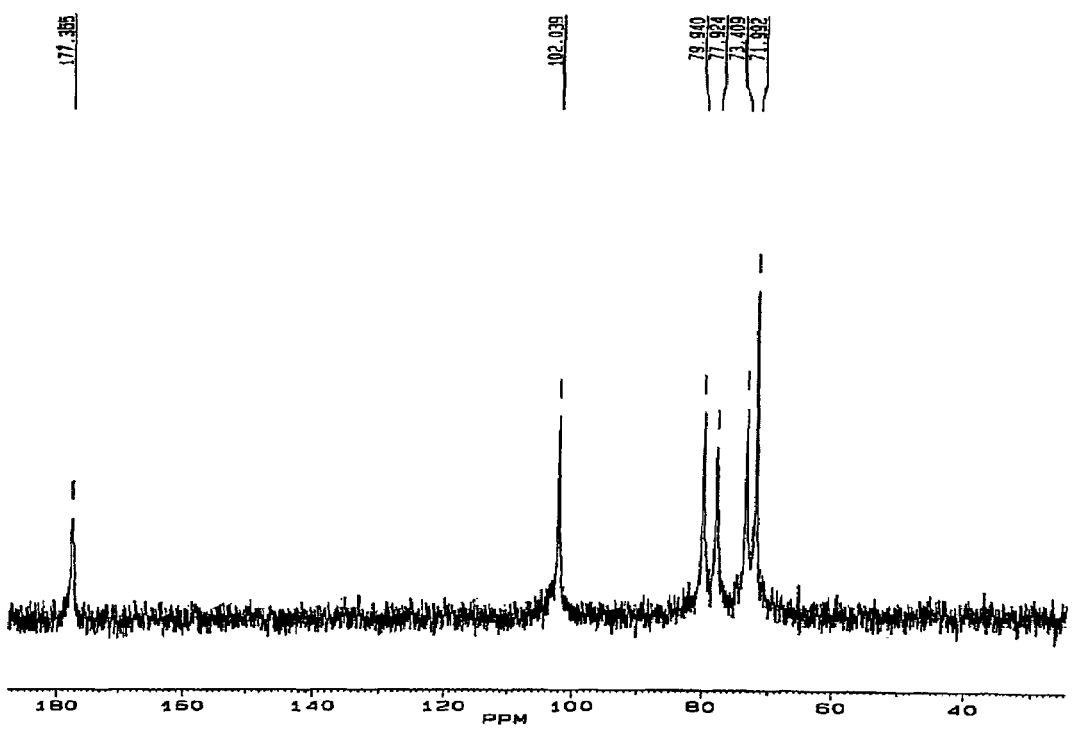
FIG. 1 represents the $^{13}$C-nuclear magnetic resonance spectrum of sodium polymannuronate.
Figure 2:
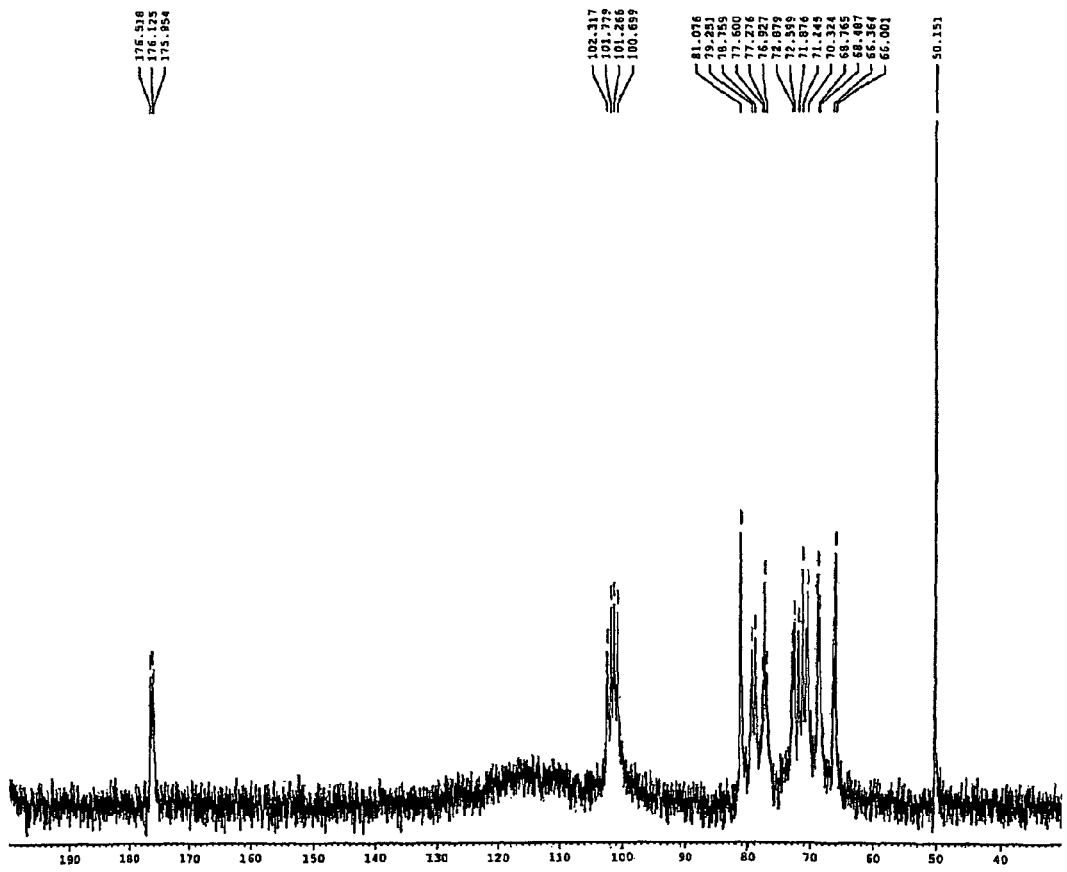
FIG. 2 represents the $^{13}$C-nuclear resonance spectrum of sodium alginate.

The following non-limiting examples illustrate the invention and do not limit its scope in any way. In the examples and throughout this specification, all percentages, parts and ratios are by weight unless indicated otherwise.

EXAMPLES

Composition and yields of first, second and third polysaccharide fractions obtained from different species of seaweeds by the method claimed are presented in Table 1.

TABLE 1

| | Polysaccharides, % from weight of dry seaweed | | | | | |
|---|---|---|---|---|---|---|
| | First polysaccharides | | Second polysaccharides | | | Third polysaccharides |
| seaweed | L1* | F1** | L2 | F2 | M*** | A**** |
| Fucus evanescens | 0.5-0.6 | 3.4-4.0 | 0.3-0.5 | 7.0-7.8 | 0.2-0.3 | 14.0-14.5 |
| Laminaria cichorioides | 4.1-5.0 | 2.0-2.5 | 6.0-6.5 | 5.0-5.5 | 0-0.1 | 18.0-19.0 |
| Laminaria japonica | 0.3-0.5 | 2.1-3.0 | 0.7-1.0 | 2.7-3.0 | 0.2-0.3 | 22.0-23.0 |
| Alaria marginata | 0-0.1 | 0.5-1.0 | 0.2-0.3 | 0.7-1.0 | 11.0-11.5 | 21.0-22.1 |
| Alaria fistulosa | 0.2-0.4 | 1.5-2.0 | 0.3-0.5 | 0 | 21.5-22.1 | 14.5-15.0 |
| Undaria pinnatifida | 0 | 3.0-3.5 | 0 | 6.0-7.0 | 2.0-3.0 | 15.0-16.0 |

L*—laminaran,
F**—fucoidan,
M***—polymannuronate,
A****—alginate

The preparations of acidic and neutral polysaccharides obtained by the method claimed were analyzed qualitatively and quantitatively by the following methods:

Phenol-sulphuric acidic method—to determine total sugars (Dubois et al, Colorimetric method for determination of sugars and related substances, Anal. Chem., 1956, Vol. 28, 350 356).

HPLC—to determine content of monosaccharides (neutral sugar). Samples of polysaccharides (5 g) were hydrolysed with 4 N HCl at 100° C. for 2 h. Monosaccharide composition of acid hydrolysis products was determined by HPLC on the carbohydrate analyzer IC-5000 Biotronik with Durrum DA-X8-11 resin, on a column 385×3.2 mm at 60° C. Detection was done by bicinchoninate method on integrating system Shimadzu C-R2 AX. Monosaccharides (Rha, Rib, Man, Fuc, Gal, Xyl, Glc) were used as standards for HPLC (Waffenschmidt S., Jaenicke L. Assay of reducing sugars in the nanomole range with 2,2'-bicinchoninate (Anal. Biochem., 1987, Vol. 165, 337-340)).

The $^{13}$C-NMR spectra were obtained on the NMR-Spectrometer Bruker-Physic WM-250 with working frequency of 62.9 MHz in $D_2O$ at 70° C.

Example 1

After removal of small shells and mechanical impurities, fresh seaweed *Fucus evanescens* (25 kg) is placed in an extractor and filled up with ethanol in the ratio of 1:1 weight/volume. The mixture is maintained at a temperature of 50° C. for 22 h. The ethanol extract is decanted, ethanol is evaporated on a rotary evaporator, and a concentrate of biologically active low-molecular substances is obtained. Ethanol obtained after evaporation is re-used.

The processed seaweed is dried, filled with 0.1 M solution of hydrochloric acid and extracted for 12 h at 20-25° C. by mixing. The extract is concentrated up to ⅕ of initial volume by ultrafiltration apparatus with a membrane, 5 kDa, then neutralized to pH 6.0 with a solution of sodium hydroxide and evaporated on a rotary evaporator up to 1 L. As result, a concentrate—first polysaccharide fraction, representing a mixture comprising laminarans and fucoidans is obtained. The concentrate is further neutralized and precipitated with two volumes of ethanol and fucoidan (F1) is obtained. The precipitate is washed out with 96% ethanol and dried. The obtained preparation of fucoidan is a cream coloured powder, well soluble in water and dimethylsulfoxide; it is not soluble in alcohol, acetone, hexane, and sulphuric ether; the ash content is 26.6%.

Laminaran (L1) is precipitated from the solution by the addition of two more volumes of ethanol, the precipitate is washed with 96% ethanol and dried. The obtained preparation of laminarans represents a powder of cream colour, soluble in water and dimethylsulfoxide; it does not dissolve in alcohol, acetone, hexane, and sulphuric ether; the ash content is 2.6%.

Then the seaweed is extracted twice with hot water by mixing for 3 h and 1.5 h, respectively, at pH 3.5-4.0. The extracts are combined, concentrated up to ¹/₁₀ initial volume on ultra filtration installation with a membrane, having pore size of 15 kDa, and evaporated on a rotary evaporator up to volume 1 L. The obtained concentrate is a second polysaccharide fraction, representing a mixture of laminaran, fucoidan and polymannuronic acids. The extract is acidified to pH 2.0-2.5 and a precipitate of polymannuronic acids is separated by centrifugation. The precipitate is dissolved in the minimal volume of 1M sodium hydroxide solution, neutralized and the precipitate of sodium polymannuronate (M) is obtained by the addition of two volumes of ethanol, washed with 96% ethanol and dried. The obtained preparation of sodium polymannuronate is a cream coloured powder, well soluble in water and dimethylsulfoxide; it is insoluble in alcohol, acetone, hexane, and sulphuric ether; the ash content is 15.0%.

The supernatant, formed after sedimentation of polymannuronic acid, is neutralized and after the addition of two volumes of ethanol, fucoidan (F2) is obtained; the precipitate is washed with 96% ethanol and dried. The obtained preparation of fucoidan is a cream coloured powder, soluble in water and dimethylsulfoxide; it is insoluble in alcohol, acetone, hexane, and sulphuric ether; the ash content is 25.0%.

The addition of two more volumes of ethanol, precipitates laminaran (L2). The precipitate is washed with 96% ethanol and dried. The obtained preparation of laminaran is a cream coloured powder, soluble in water and dimethylsulfoxide; it is insoluble in alcohol, acetone, hexane, and sulphuric ether; the ash content is 2.1%.

After that the rest of the seaweed is treated with 1% a solution of sodium bicarbonate and is extracted for 3 h at temperature 65° C. The extract is concentrated threefold from its initial volume by ultrafiltration installation with a membrane, having pore size of 100 kDa, after that the extract is neutralized and after addition of two volumes of ethanol the third polysaccharide fraction, representing sodium alginate (A), is obtained. The precipitate is washed with 96% ethanol and dried. The obtained preparation of sodium alginate is a brown coloured powder, soluble in water and dimethylsulfoxide; it is insoluble in alcohol, acetone, hexane, and sulphuric ether; the ash content is 18.0%.

Table 2 shows the yield, the content of monosaccharides and the molecular weight of polysaccharides from *Fucus evanescens*.

TABLE 2

| Polysaccharide | Yield | | content of monosaccharides (neutral sugars), % | | | | | Fuc/$SO_4^{2-}$ mole/mole | Mm, kDa |
| --- | --- | --- | --- | --- | --- | --- | --- | --- | --- |
| | g | % | mannose | fucose | galactose | xylose | glucose | | |
| L1 | 14.5 | 0.6 | 0 | 0 | 0 | 3 | 89 | | 5-10 |
| F1 | 73.0 | 3.4 | 1 | 74 | 11 | 6 | 4 | 1:(0.7-1) | 20-500 |
| L2 | 12.5 | 0.5 | 0 | 0 | 0 | 0 | 100 | | 5-10 |
| F2 | 177.0 | 7.1 | 4 | 82 | 4 | 3 | 0 | 1:(0.8-1) | 15-500 |
| M | 7.5 | 0.3 | 0 | 0 | 0 | 0 | 0 | | 30-40 |
| A | 360.0 | 14.4 | 0 | 0 | 0 | 0 | 0 | | 150-500 |

Example 2

Frozen seaweed *Laminaria cichorioides* (25 kg) is prepared for extraction and is extracted with ethanol, as described in Example 1.

Processed seaweed is dried, treated in with 0.1 M solution of a hydrochloric acid and is extracted for 12 h at 20-25° C. by mixing the reaction mixture. The extract is concentrated up to ⅕ of initial volume on ultrafiltration apparatus with a membrane, having pore size of 5 kDa, then is neutralized up to pH 6.0 with sodium hydroxide solution and evaporated on a rotary evaporator up to 1 L. The obtained concentrate—first polysaccharide fraction, represents a mixture of laminaran and fucoidan. The concentrate is neutralized and precipitated with two volumes of ethanol, which gives fucoidan (F1). The precipitate is washed with 96% ethanol and dried. The obtained preparation of fucoidan is a cream coloured powder, soluble in water and dimethylsulfoxide; it is not soluble in alcohol acetone, hexane, and sulphuric ether; the ash content is 21.0%.

By addition of two more volumes of ethanol to the supernatant, laminaran (L1) is precipitated. The precipitate is washed with 96% ethanol and dried. The obtained preparation of laminaran is a white coloured powder, soluble in water and dimethylsulfoxide; it is insoluble in alcohol, acetone, hexane, and sulphuric ether; the ash content is 2.2%.

All subsequent stages are carried on as described in Example 1, with the exception of alkaline processing, which is carried out with 1% a solution of ammonium oxalate. Win this step, an ammonium alginate preparation is obtained as a cream coloured powder, soluble in water and dimethylsulfoxide; it is insoluble in alcohol, acetone, hexane, and sulphuric ether; the ash content is 15.0%.

In Table 3 the structure characteristics and molecular weight of polysaccharides from *Laminaria cichorioides* and content of monosaccharides are presented

TABLE 3

| Polysaccharide | Yield g | Yield % | mannose | fucose | galactose | xylose | glucose | Fuc/SO$_4^{2-}$ mol/mol | Mr, kDa |
|---|---|---|---|---|---|---|---|---|---|
| L1 | 102.0 | 4.1 | 0 | 0 | 0 | 0 | 97 |  | 5-10 |
| F1 | 62.5 | 2.5 | 1 | 90 | 1 | 0 | 5 | 1:(1.6-1.8) | 20-40 |
| L2 | 152.1 | 6.1 | 0 | 0 | 0 | 0 | 100 |  | 5-10 |
| F2 | 127.2 | 5.1 | 0 | 92 | 6 | 0 | 0 | 1:(1.8-2) | 20-30 |
| M | 2.8 | 0.1 | 0 | 0 | 0 | 0 | 0 |  | 30-40 |
| A | 450.3 | 18.0 | 0 | 0 | 0 | 0 | 0 |  | 150-500 |

Example 3

Fresh seaweeds *Laminaria japonica* (25 kg) is prepared for extraction and is extracted with ethanol in the same way as in Example 1.

Processed seaweed is dried, filled with 0.1 M solution of a hydrochloric acid and extracted for 12 h at 20-25° C. with mixing the reaction mixture. The extract is concentrated up to ⅕ of initial volume on ultrafiltration apparatus with a membrane, having a pore size of 5 kDa, then the extract is neutralized up to pH 6.0 with sodium hydroxide and evaporated on a rotary evaporator up to 1 L. The obtained concentrate, first polysaccharide fraction, represents a mix of laminaran and fucoidan. The concentrate is neutralized and after precipitation with two volumes of ethanol the fucoidan (F1) is obtained. The precipitate is washed with 96% ethanol and dried. The resulting preparation of fucoidan is a cream coloured powder, well soluble in water and dimethylsulfoxide; it is not soluble in alcohol, acetone, hexane, and sulphuric ether; the ash content is 17.0%.

All subsequent stages are carried out as described in Example 1, but alkaline processing is carried out with 1% calcium hydroxide. The resulting calcium alginate is a cream coloured powder, which forms viscous gels on dissolution in water; the ash content is 17.0%.

Table 4 shows the structure characteristics and molecular weight of polysaccharides from *Laminaria japonica* and the content of monosaccharides.

Example 4

Frozen seaweed *Alaria marginata* (25 kg) is prepared for extraction and is extracted with ethanol in the same way as in Example 1.

Processed seaweeds are dried, filled with 0.1 M solution of a hydrochloric acid and extracted for 12 h at 20-25° C. with mixing the reaction mixture. The extract is concentrated up to ⅕ of initial volume on ultrafiltration apparatus with a membrane, having a pore size of 5 kDa, then the extract is neutralized up to pH 6.0 with sodium hydroxide and evaporated on a rotary evaporator up to 1 L. Thereafter, the seaweed is treated in the same way as in Example 1.

The obtained preparation of fucoidan (F1 and F2) is a cream coloured powder, well soluble in water and dimethylsulfoxide; it is not dissolved in alcohol, acetone, hexane, and sulphuric ether; the ash content is 19.0%.

The seaweed is further processed, as is described in an Example 1, but the precipitate of polymannuronic acid is dissolved in a minimal volume of 1M solution of calcium hydroxide, then it is neutralized and calcium polymannuronate (PM) is precipitated. The obtained preparation of calcium polymannuronate is a white powder, soluble in water and dimethylsulfoxide; it is insoluble in alcohol, acetone, hexane, a sulphuric ether; the ash content is 17.0%.

The seaweed is subsequently further processed as described in Example 1. The resulting preparation of sodium alginate is a brown coloured powder, soluble in water and dimethylsulfoxide; it is not soluble in alcohol, acetone, hexane, a sulphuric ether; the ash content is 18.0%.

Table 5 shows the structure characteristics and molecular weight of polysaccharides from *Alaria marginata* and the content of monosaccharides.

TABLE 4

| Polysaccharide | Yield g | Yield % | mannose | fucose | galactose | xylose | glucose | Fuc/SO$_4^{2-}$ mol/mol | Mr, kDa |
|---|---|---|---|---|---|---|---|---|---|
| L1 | 7.7 | 0.3 | 0 | 0 | 3 | 5 | 90 |  | 4-5 |
| F1 | 53.0 | 2.1 | 2 | 44 | 25 | 10 | 5 | *n.d. | n.d. |
| L2 | 21.5 | 0.9 | 0 | 0 | 0 | 0 | 92 |  | 5-10 |
| F2 | 72.0 | 2.9 | 0.3 | 39.5 | 46.0 | 0 | 0.9 | 1:1.1 | n.d. |
| M | 5.7 | 0.2 | 0 | 0 | 0 | 0 | 0 |  | 30-40 |
| A | 560.3 | 22.4 | 0 | 0 | 0 | 0 | 0 |  | 150-500 |

*n.d.—not determined

TABLE 5

| Polysaccharide | Yield | | content of monosaccharides (neutral sugars, %) | | | | | Fuc/SO$_4^{2-}$ | Mr, kDa |
| --- | --- | --- | --- | --- | --- | --- | --- | --- | --- |
| | g | % | mannose | fucose | galactose | xylose | glucose | mol/mol | |
| L1 | 2.5 | 0.1 | 0 | 0 | 0 | 0 | 92 | | n.d. |
| F1 | 42.0 | 1.7 | 2 | 72 | 6 | 8 | 5 | *n.d. | n.d. |
| L2 | 7.5 | 0.3 | 0 | 0 | 0 | 0 | 93 | | n.d. |
| F2 | 20.0 | 0.8 | 4 | 68 | 8 | 10 | 3 | n.d. | n.d. |
| M | 275.0 | 11.0 | 0 | 0 | 0 | 0 | 0 | | 30-40 |
| A | 537.5 | 21.5 | 0 | 0 | 0 | 0 | 0 | | 150-500 |

Example 5

Frozen seaweed *Alaria fistulosa* (25 kg) is prepared for extraction and is extracted with ethanol in the same way as in Example 1.

Processed seaweed is dried, treated with 0.1 M solution of a hydrochloric acid and extracted for 12 h at 20-25° C. with mixing the reaction mixture. The extract is concentrated up to ⅕ of initial volume on ultrafiltration apparatus with a membrane, having pore size of 5 kDa, then the extract is neutralized up to pH 6.0 with sodium hydroxide and evaporated on a rotary evaporator up to 1 L.

Further processing is carried out, as described in Example 1, but the precipitate of polymannuronic acid is dissolved in a minimal volume of 1M solution of ammonium oxalate, then it is neutralized and ammonium polymannuronate (PM) is precipitated. The obtained ammonium polymannuronate is a white powder, soluble in water and dimethylsulfoxide; it is not dissolved in alcohol, acetone, hexane, and sulphuric ether; the ash content is 21.0%.

Further processing of the seaweed is carried out, as described in Example 1.

Table 6 shows the structure characteristics and molecular weight of polysaccharides from *Alaria fistulosa* and the content of monosaccharides.

Processed seaweed is dried, treated with 0.1 M solution of hydrochloric acid and extracted for 12 h at 20-25° C. with mixing. The extract is concentrated up to ⅕ of initial volume on ultrafiltration apparatus with a membrane, having a pore size of 5 kDa, then the extract is neutralized with sodium hydroxide and evaporated on a rotary evaporator up to 1 L. The seaweed is treated further as described in Example 1.

The obtained preparation of fucoidan (F1 and F2) is a white coloured powder, soluble in water and dimethylsulfoxide; it is not soluble in alcohol, acetone, hexane, and sulphuric ether; the ash content is 30.0%.

Further processing is carried out as described in Example 1, but the precipitate of polymannuronic acids is dissolved in a minimal volume of 1 M solution of magnesium hydroxide, then it is neutralized and magnesium polymannuronate (PM) is precipitated. The resulting preparation of magnesium polymannuronate is a white coloured powder, soluble in water and dimethylsulfoxide; it is not soluble in alcohol, acetone, hexane, and sulphuric ether; the ash content is 19.0%.

Further processing is carried out as described in Example 1, but alkaline treatment of seaweed is carried out with 1% solution of magnesium hydroxide and magnesium alginate (A) is obtained. The resulting preparation of magnesium alginate is a cream coloured powder, soluble in water and dim-

TABLE 6

| Polysaccharide | Yield | | content of monosaccharides (neutral sugars, %) | | | | | Fuc/SO$_4^{2-}$ | Mr, kDa |
| --- | --- | --- | --- | --- | --- | --- | --- | --- | --- |
| | g | % | mannose | fucose | galactose | xylose | glucose | mol/mol | |
| L1 | 10.0 | 0.4 | 0 | 0 | 0 | 0 | 92 | | n.d. |
| F1 | 44.5 | 1.8 | 1 | 75 | 7 | 8 | 5 | *n.d. | n.d. |
| L2 | 12.5 | 0.5 | 0 | 0 | 0 | 0 | 94 | | n.d. |
| F2 | 0 | 0 | | | | | | | |
| M | 552.5 | 22.1 | 0 | 0 | 0 | 0 | 0 | | 30-40 |
| A | 375.3 | 15.0 | 0 | 0 | 0 | 0 | 0 | | 150-500 |

Grams of % mannose, fructose, galactose, xylose, glucose
*n.d.—not determined

Example 6

Fresh seaweed *Undaria pinnatifida* (25 kg) is prepared for extraction and is extracted with ethanol the same way as in Example 1.

ethylsulfoxide; it is not soluble in alcohol, acetone, hexane, and sulphuric ether; the ash content is 20.0%.

Table 7 shows the structure characteristics and molecular weight of polysaccharides from *Undaria pinnatifida* and the content of monosaccharides.

TABLE 7

| Polysaccharide | Yield | | content of monosaccharides (neutral sugars, %) | | | | |
| --- | --- | --- | --- | --- | --- | --- | --- |
| | g | % | mannose | fucose | galactose | xylose | glucose |
| L1 | 0 | 0 | 0 | 0 | 0 | 0 | 0 |
| F1 | 77.0 | 3.1 | 1 | 44 | 51 | 0 | 0 |
| L2 | 0 | 0 | 0 | 0 | 0 | 0 | 0 |
| F2 | 152.0 | 6.1 | 0.3 | 39.5 | 46.0 | 0 | 0.9 |
| M | 58.0 | 2.3 | 0 | 0 | 0 | 0 | 0 |
| A | 375.3 | 15.0 | 0 | 0 | 0 | 0 | 0 |

The invention claimed is:

1. A method of processing seaweed which comprises the following steps:
   (i) treating seaweed with an alcohol having one to six carbon atoms to form an alcoholic fraction and an insoluble first seaweed residue;
   (ii) separating the alcoholic fraction;
   (iii) removing the alcohol from the alcoholic fraction to form a concentrate comprising biologically active compounds;
   (iv) extracting the first seaweed residue with an aqueous solution at a pH of less than about 6 to form an aqueous first extract and an insoluble second seaweed residue;
   (v) optionally concentrating the first extract;
   (vi) adjusting the pH of the first extract (iv) or the concentrated extract of (v) to a value in the range of about 5 to about 8 to obtain a first polysaccharide fraction comprising a mixture of laminaran and fucoidan;
   (vii) extracting the second seaweed residue with water at a temperature of 40 to 100° to form an aqueous second extract and an insoluble third seaweed residue;
   (viii) concentrating the second extract; and drying the concentrate to obtain a second polysaccharide fraction comprising a mixture of laminaran, fucoidan, and polymannuronic acid; and
   (ix) acidifying the second polysaccharide fraction to a pH not higher than 2.5 to precipitate polymannuronic acid; and separating the polymannuronic acid.

2. The method as claimed in claim 1, further comprising treating the first polysaccharide fraction with ethanol to sequentially precipitate fucoidan first and then laminaran.

3. The method as claimed in claim 1, further comprising dissolving the precipitate in an alkaline solution and precipitating a salt of polymannuronic acid with ethanol.

4. The method as claimed in claim 3, further comprising: neutralizing the supernatant after precipitation; and precipitating the neutralized supernatant with ethanol to form a third polysaccharide fraction comprising fucoidan and laminaran.

5. The method as claimed in claim 4, further comprising treating the third seaweed residue of (vii) with an alkali to form a third extract.

6. The method as claimed in claim 5, further comprising concentrating and neutralizing the third extract and precipitating with ethanol to obtain a further polysaccharide fraction comprising a salt of alginic acid.

7. The method as claimed in claim 6, wherein the seaweed is a brown seaweed.

8. The method as claimed in claim 7, wherein the seaweed is from a species selected from the group consisting of *Laminaria cichorioides, Laminaria japonica, Alaria marginata, Alaria fistulosa, Fucus evanescens* and *Undaria pinnatifida*.

9. The method as claimed in claim 8, wherein the seaweed is frozen.

10. The method as claimed in claim 9, wherein in (i), the seaweed is treated with ethanol at a temperature of from about 40 to about 60° C.

11. The method as claimed in claim 3, wherein a salt of polymannuronic acid is formed by treating the precipitate of polymannuronic acid with a solution of a compound selected from the group consisting of sodium hydroxide, ammonium oxalate, calcium hydroxide and magnesium hydroxide.

12. The method as claimed in claim 11 wherein the salt is sodium hydroxide.

13. The method as claimed in claim 6, wherein a salt of alginic acid is formed by treating the third seaweed residue with a compound selected from the group consisting of sodium hydroxide, sodium bicarbonate, ammonium oxalate, calcium hydroxide and magnesium hydroxide.

14. The method as claimed in claim 13 wherein the salt is sodium bicarbonate.

15. The method as claimed in claim 1, wherein in (iv) the first seaweed residue is extracted from hydrochloric acid at pH of about 0.5-3.0.

16. The method as claimed in claim 1, wherein the second seaweed residue is extracted with water at pH of about 2.0-5.0.

17. The method as claimed in claim 16, including the further step of concentrating one or more of the extracts by ultrafiltration on hollow fiber with pore size of 6-100 kDa.

18. The method as claimed in claim 1 wherein the alcohol is ethanol and the seaweed is *Fucus evanescens*.

\* \* \* \* \*

UNITED STATES PATENT AND TRADEMARK OFFICE
CERTIFICATE OF CORRECTION

| | | |
|---|---|---|
| PATENT NO. | : 7,611,716 B2 | Page 1 of 1 |
| APPLICATION NO. | : 10/566133 | |
| DATED | : November 3, 2009 | |
| INVENTOR(S) | : Michailovna et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 389 days.

Signed and Sealed this

Twelfth Day of October, 2010

David J. Kappos
*Director of the United States Patent and Trademark Office*